United States Patent [19]

Nishimura et al.

[11] Patent Number: 5,427,959
[45] Date of Patent: Jun. 27, 1995

[54] APPARATUS AND METHOD FOR MEASURING SPECIMEN

[75] Inventors: Matsuomi Nishimura, Ohmiya; Kazumi Tanaka, Yokohama; Takeshi Miyazaki, Ebina; Hidehito Takayama, Chigasaki; Toshikazu Ohnishi, Machida, all of Japan

[73] Assignee: Canon Kabushiki Kaisha, Tokyo, Japan

[21] Appl. No.: 769,366

[22] Filed: Oct. 1, 1991

[30] Foreign Application Priority Data

| Oct. 1, 1990 | [JP] | Japan | 2-263280 |
| Mar. 18, 1991 | [JP] | Japan | 3-78431 |
| Jun. 5, 1991 | [JP] | Japan | 3-161070 |
| Aug. 30, 1991 | [JP] | Japan | 3-246929 |
| Aug. 30, 1991 | [JP] | Japan | 3-246930 |

[51] Int. Cl.6 .................................... G01N 33/546
[52] U.S. Cl. ............................ 436/534; 356/244; 356/246; 422/58; 422/72; 422/73; 422/101; 422/102; 436/164; 436/165; 436/172; 436/531; 436/533; 436/536; 436/538; 436/541; 436/805; 436/807; 436/808; 436/809; 436/810; 436/824; 436/908
[58] Field of Search ............... 422/58, 72, 73, 99, 422/101, 102; 436/45, 164, 165, 172, 531, 534, 536, 538, 541, 805, 807, 808-810, 824, 908, 69, 70, 518, 520, 521, 533; 356/244, 246

[56] References Cited

U.S. PATENT DOCUMENTS

| 3,492,396 | 1/1970 | Dalton et al. | 436/541 |
| 3,718,431 | 2/1973 | Wild | 422/58 |
| 4,088,448 | 5/1978 | Lilja et al. | 422/57 |
| 4,425,438 | 1/1984 | Bauman et al. | 436/541 |
| 4,596,695 | 6/1986 | Cottingham | 422/58 |
| 4,661,460 | 4/1987 | Sakuma | 436/534 |
| 4,720,465 | 1/1988 | Jensen et al. | 436/534 |
| 4,721,681 | 1/1988 | Lentrichia et al. | 436/534 |
| 4,745,075 | 5/1988 | Hadfield et al. | 436/523 |
| 4,790,640 | 12/1988 | Nason | 356/246 |
| 4,952,520 | 8/1990 | Okusa et al. | 436/534 |

FOREIGN PATENT DOCUMENTS

| 0266894 | 5/1988 | European Pat. Off. |
| 0293779 | 12/1988 | European Pat. Off. |
| 3522098 | 1/1987 | Germany |

Primary Examiner—Toni R. Scheiner
Assistant Examiner—Christopher L. Chin
Attorney, Agent, or Firm—Fitzpatrick, Cella, Harper & Scinto

[57] ABSTRACT

On a slab-like board formed of a transparent material is closely attached a wedge-shaped transparent cover member provided with a recess in a central inner portion, thereby to form a clearance. The height of the clearance between the recess and the board is configured to decrease continuously or in steps. When an immunological active substance such as a monoclonal antibody is caused to sensitize carrier particles F, and a reagent having the carrier particles F dispersed into a liquid medium mainly composed of the water is mixed with a specimen, the reaction will occur in which the flocculate is formed from plural carrier particles. When this reaction liquid is poured into the clearance through the opening, the reaction liquid penetrates in the direction having a narrower vertical spacing due to surface tension. A single carrier particle unflocculated can move deep within the recess because it is small in diameter, but the flocculate G is trapped on its way and can not move because of its size.

20 Claims, 17 Drawing Sheets

F I G. 33
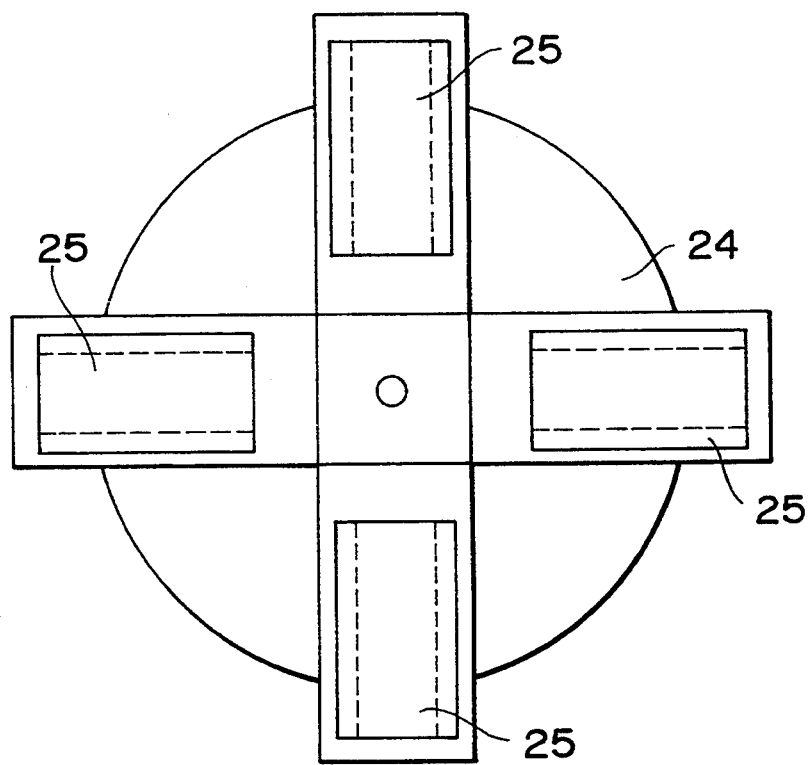

APPARATUS AND METHOD FOR MEASURING SPECIMEN

BACKGROUND OF THE INVENTION

1. Field of the Invention

The present invention relates to a specimen measuring apparatus for detecting a specified substance in a specimen qualitatively or quantitatively.

2. Related Background Art

For detecting a specified substance in a specimen, for example, an immunological active substance such as antigen or antibody, there is known a method in which the immunological active substance is detected qualitatively by observing and confirming the flocculation state of a reaction liquid where the immunological active substance such as monoclonal antibody is caused to sensitize carrier particles of colloid or the like such as latex particles, glass particles, ceramic balls, kaoline, carbon black, or animal blood constituents such as red blood cells, and then the carrier particles are reacted with the specimen in a liquid medium.

However, in said conventional embodiment, the detection may be too poor in quantitativeness to judge the flocculation state visually, resulting in a lack of the accuracy and reliability of detection.

SUMMARY OF THE INVENTION

It is an object of the present invention provide a specimen measuring apparatus capable of making the qualitative and quantitative detection at high accuracy and with a simple structure.

BRIEF DESCRIPTION OF THE DRAWINGS

FIG. 33 is a plan view of a thirteenth embodiment.

DESCRIPTION OF THE PREFERRED EMBODIMENTS

Figure 1:
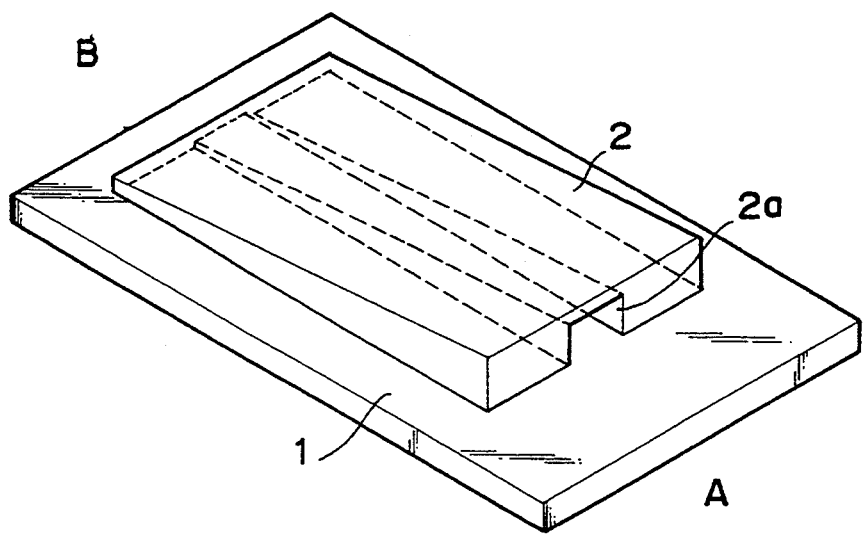
FIG. 1 is a perspective view of a first embodiment.

The present invention will be described below in detail based on the embodiments in the drawings.

Figure 2:
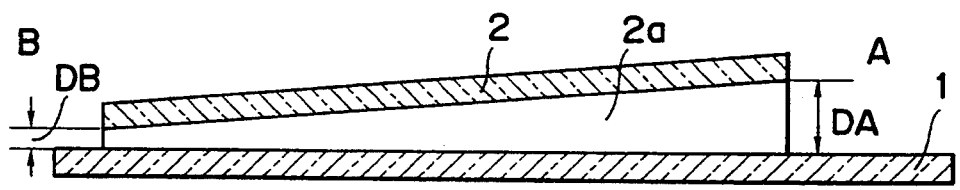
FIG. 2 is a longitudinal cross-sectional view of FIG. 1.

FIG. 1 is an external perspective view of a sample stand in a first embodiment, and FIG. 2 is a longitudinal cross-sectional view taken along a direction A–B of FIG. 1. On a slab-like base board 1 formed of a transparent material is closely attached a wedge-shaped cover member 2 formed of a transparent material and provided with a recess 2a in a central inner portion, thereby to form a clearance. The recess 2a is such that the height of clearance between the recess 2a and the board 1 decreases continuously from direction A toward direction B, as shown in FIG. 2, with a vertical spacing DB of an opening at an end portion being smaller than the diameter R of carrier particle F for use, and a vertical spacing DA of an opening at a directional end portion being about several to hundreds times the vertical spacing DB so as to pass the flocculate G therethrough.

Figure 3:
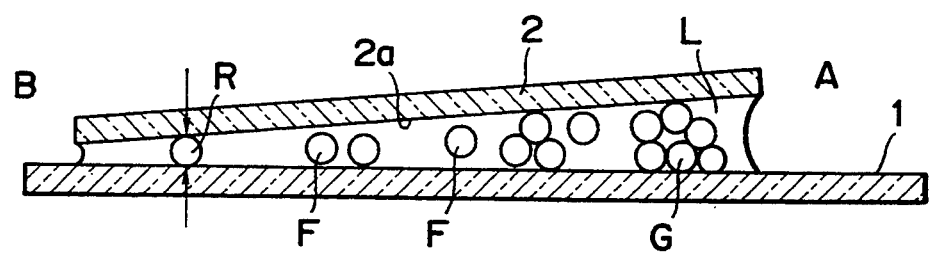
FIG. 3 is an explanation view of a measuring principle for the first embodiment.

An immunological active substance such as monoclonal antibody is caused to sensitize colored carrier particles F, and a reagent with the carrier particles F dispersed into a liquid medium mainly composed of the water is mixed with a specimen such as serum. Then, the antigen-antibody reaction will occur when there exists the antigen specifically reacting to the monoclonal antibody in the serum. Wherein the flocculate G is formed by plural immunological active substances and carrier particles F. After sufficient reaction, when this reaction liquid L is poured into the clearance between the board 1 and the recess 2a from the direction A, as shown in FIG. 3, the reaction liquid L penetrates in the direction B having a narrower vertical spacing due to surface tension. A single carrier particle F unflocculated can move deep into the direction B because it is small in diameter, but the flocculate G is trapped on its way and can not move because of its size.

The diameter of flocculate G determined by the number of carrier particles F constituting one flocculate G and the number of flocculates G trapped in a certain spacing have a correlation with the property and number of immunological active substances contained in the reaction liquid L, i.e., the flocculation state of flocculates G generated by the reaction. Accordingly, if the reaction liquid L flows into such clearance, the quantity of carrier paricles F trapped in the clearance R equal to the diameter R of single carrier particle F, the position at which the flocculate G is trapped and its quantity can be easily determined and discriminated visually, whereby the immunological active substance can be detected qualitatively and quantitatively. In practice, an analytical curve is made beforehand by the reaction liquid L reacted with a specimen for analysis containing a known immunological active substance, and the determination is made by the comparison with that curve.

Either the board 1 or the cover member 2 can be of an opaque member, or have a color tone facilitating the discrimination in accordance with the color tone of colored carrier particle F. For example, if the carrier particle F is a bright color, the member is formed in a dark color so as to make the discrimination easier. Also, if a substance having a good affinity with the liquid medium of reaction liquid L is coated on a surface of the clearance so that the reaction liquid L may easily enter the clearance, a further excellent measuring result can be obtained. This coating material is preferably a hydrophilic substance, a surfactant, or a water-soluble high polymer such as methylcellulose, carboxymethylcellulose, polyvinyl alcohol and polyacrylamide, if the liquid medium is water, for example.

Also, the measurement can be further effectively made if the carrier particle F is made to emit a fluorescence. The carrier particle emitting the fluorescence can be obtained by the following method, for example. The material of a carrier particle may be a polymer particle, a glass particle, a ceramic ball, a kaoline or carbon black, as conventionally used, and among them the polymer particle is more preferable because it easily made to be a fluorescent particle. The fluorescent particle can be appropriately obtained with use of the material of a carrier particle and the kind of fluorescent matter. Giving an embodiment of a polymer particle such as polystyrene, polyacrylic ester, polyester, polycarbonate or polyamide, there is a method of mixing the polymer particle with a substance having the fluorescent property, for example, a fluorescence dye and then fixing the fluorescence dye with the chemical or physical bonding, or fusing and kneading the polymer particle and the fluorescence dye.

Figure 4:
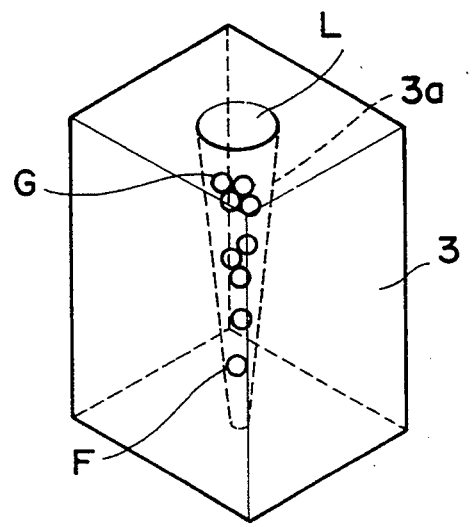
FIG. 4 is a perspective view of a modification of the first embodiment.

In this embodiment, the reaction liquid L is poured in a horizontal direction with the board 1 installed horizontally, but the board 1 can be erected vertically with the direction A placed upward as shown in FIG. 1 to make the measurement, wherein the ingress of the reaction liquid L is facilitated due to the effect of gravity, whereby an excellent measurement result can be obtained. This can be also achieved by providing a clearance 3a having the diameter continuously decreasing downward within a base, body 3 which is partially transparent, as shown in FIG. 4.

Figure 5:
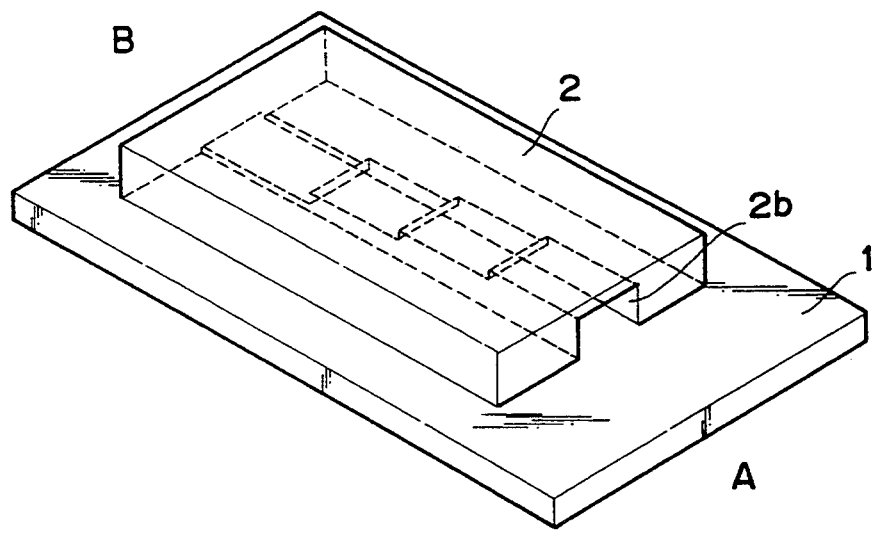
FIG. 5 is a perspective view of a second embodiment.
Figure 6:
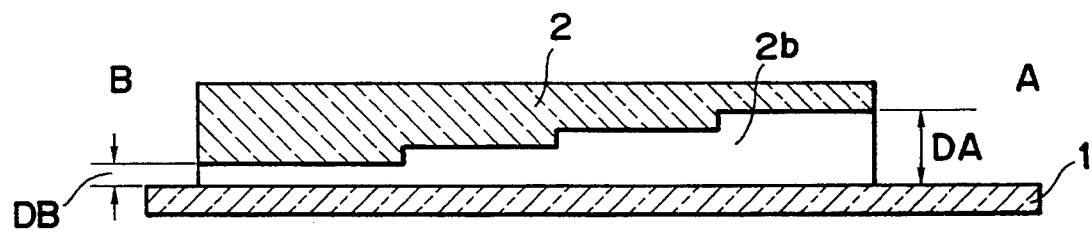
FIG. 6 is a longitudinal cross-sectional view of FIG. 5.

FIG. 5 is a constitutional view of a sample stand in the second embodiment, and FIG. 6 is a longitudinal cross-sectional view taken along direction A–B of FIG. 5. On a slab-like board 1 formed of a transparent material is closely attached a slab-like cover member 2 formed of transparent material and provided with a recess 2b in a central inner portion, thereby to form a clearance. The recess 2b is such that the height of clearance between the recess 2b and the board 1 decreases in four steps, for example, from the direction A to the direction B, as shown in FIG. 6, with a vertical spacing DB of an opening at an end portion in the direction B being smaller than the diameter of carrier particle F for use, and a vertical spacing DA of an opening at an end portion in the direction A being about several to hundreds times the vertical spacing DB so as to pass the flocculate G therethrough.

Figure 7:
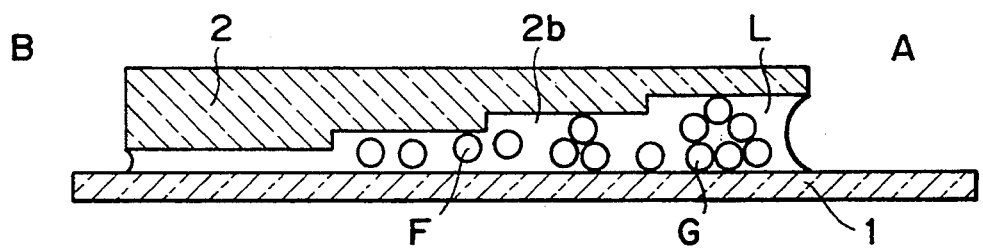
FIG. 7 is an explanation view of a measuring principle for the second embodiment.
Figure 8:
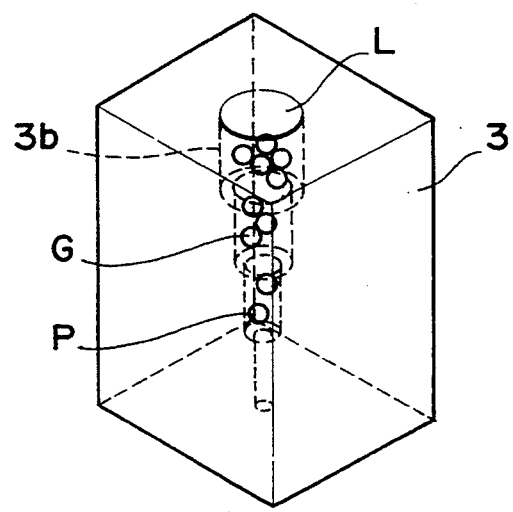
FIG. 8 is a perspective view of a modification of the second embodiment.

In this embodiment, when the reaction liquid L is poured from the direction A, the immunological active substance can be similarly detected qualitatively and quantitatively because the flocculate G is trapped on its way, as shown in FIG. 7. For its purpose, the vertical spacing of the recess 2b must be changed in at least three steps. Also, as in the first embodiment, the board 1 may be erected vertically for its use, wherein a clearance 3b having the diameter decreasing in steps in a downward direction can be vertically provided inside of a base body 3 as shown in FIG. 8.

Figure 9:
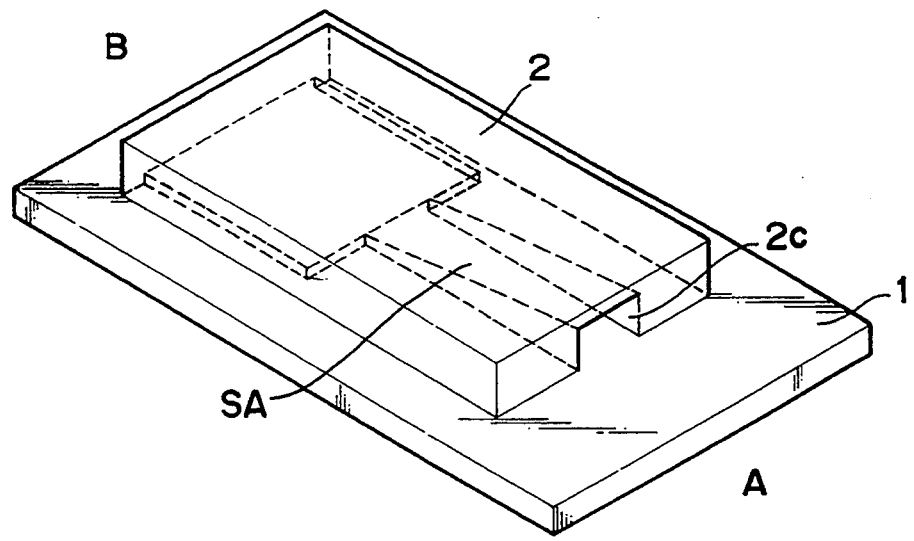
FIG. 9 is a perspective view of a third embodiment.
Figure 10:
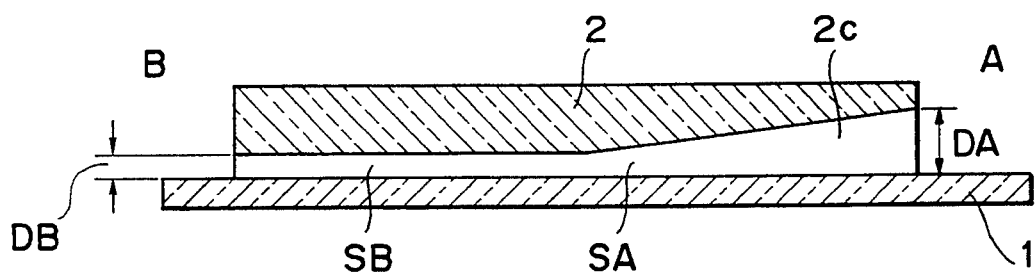
FIG. 10 is a longitudinal cross-sectional view of FIG. 9.

FIG. 9 is a constitutional view of the third embodiment, and FIG. 10 is a longitudinal cross-sectional view taken along direction A–B of FIG. 9. As the first and second embodiments, on a slab-like board 1 formed of a transparent material is closely attached a slab-like cover member 2 formed of a transparent material and provided with a recess 2c in a central inner portion, thereby to form a clearance. The recess 20 comprises the clearance with the vertical distance between a recess 2c and the board 1 decreasing continuously from the direction A toward the direction B, as shown in FIG. 10, with the width of the clearance being fixed from the position of a vertical spacing DB being smaller than the diameter of carrier particle F for use, and the volume of a clearance portion SB of the vertical spacing DB being substantially equal to or greater than that of a clearance portion SA having a larger vertical spacing than the vertical spacing DB. The vertical spacing DA of an opening at an end portion in the direction A being about several to hundreds times the vertical spacing DB so as to pass the flocculate G therethrough.

In this embodiment, when the reaction liquid L is poured into the clearance between the board 1 and the cover member 2 from the direction A, the reaction liquid L enters toward direction B having a narrower vertical spacing, the carrier particle or flocculate G is trapped at the position corresponding to its diameter. Only the mixed liquid of a liquid medium and a specimen move to the clearance portions SB having a vertical spacing DB. Since the clearance portion SB has a larger volume, most of the mixed liquid unnecessary for the detection flows into that portion, wherein the clearance portion SA having a larger vertical spacing allows for easy detection of carrier particles F and flocculate G trapped, and an excellent result can be obtained. The clearance of vertical spacing DB may be arbitrarily shaped if the volume condition can be satisfied.

Figure 11:
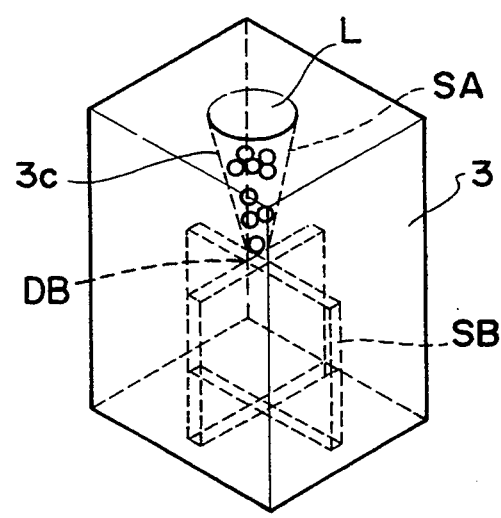
FIG. 11 is a perspective view of a modification of the third embodiment.

Also, in this embodiment, the reaction liquid may be poured into a vertical direction, with the board 1 erected vertically, wherein the same advantages can be obtained to such a manner that a base body 3 is constituted to have the diameter continuously decreasing from an upper side thereof, and comprise a clearance portion SB of which the sections are orthogonally formed extending at the spacing DB in both directions from the position having the spacing DB smaller than the diameter of carrier particle F, as shown in FIG. 11, whereby the carrier particle F is trapped at a clearance portion SA larger than the diameter DB while only the mixed liquid of the liquid medium and the specimen flows into the clearance portion SB located below. In this case, the clearance portion SB under the position of the diameter DB can be of any shape, if the above condition of the volume can be satisfied, even with its spacing being below DB.

Figure 12:
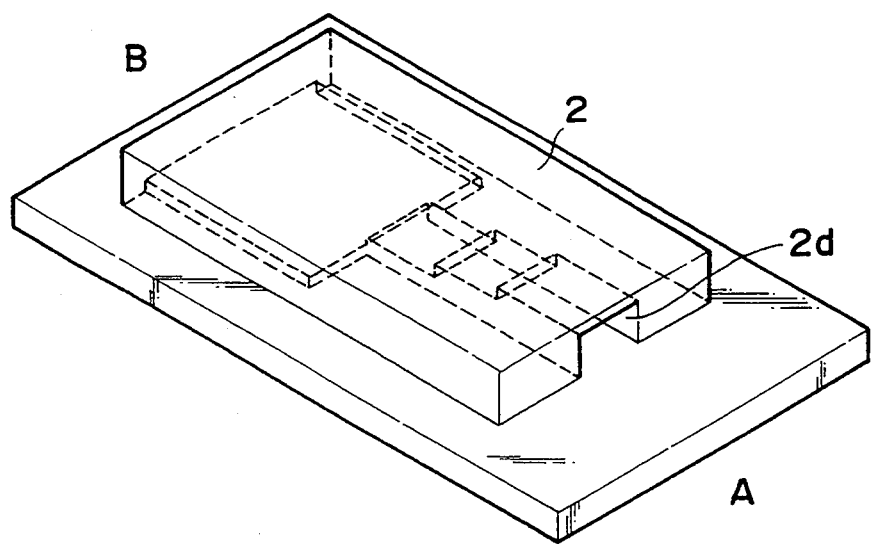
FIG. 12 is a perspective view of a fourth embodiment.

FIG. 12 is a constitutional view of the fourth embodiment, with a recess 2d of the cover member 2 having three steps of the height in the clearance portion SA formed as in FIG. 9, and the clearance portion SB having the clearance DB provided behind.

Figure 13:
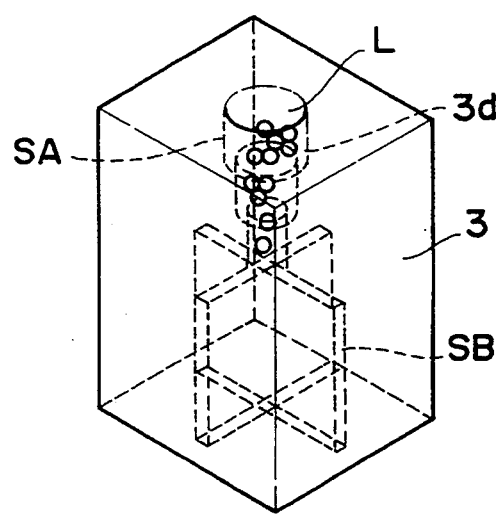
FIG. 13 is a perspective view of a modification of the fourth embodiment.

In this embodiment, the effects with the second and third embodiments combined can be obtained. A clearance 3d may be varied vertically by the base body 3, as shown in FIG. 13.

By the way, in the third and fourth embodiments, the vertical spacing SB may be set slightly larger than the diameter F of carrier particle F, for example, less than two times. In this case, unflocculated particles or carrier particles F are not trapped but absorbed into the clearance portion SB, so that the flocculation or nonflocculation can be judged more clearly and easily, and a further excellent measurement result can be obtained.

Figure 14:
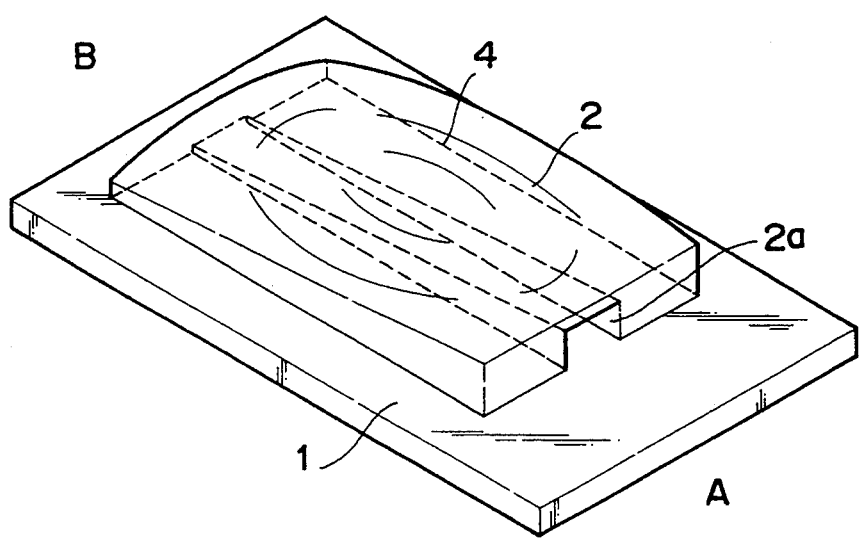
FIG. 14 is a perspective view of a fifth embodiment.
Figure 15:
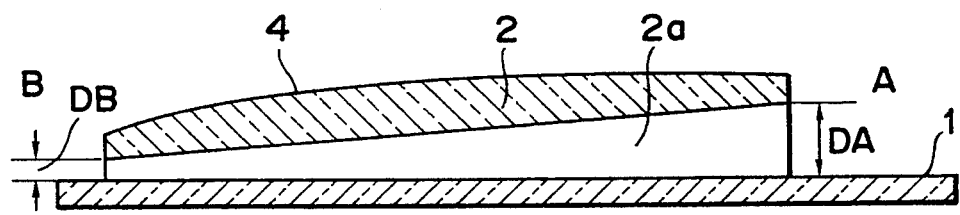
FIG. 15 is a longitudinal cross-sectional view of FIG. 14.

FIG. 14 is an external perspective view of the fifth embodiment, and FIG. 15 is a longitudinal cross-sectional view taken along the direction A-B of FIG. 14. This has a convex lens 4 formed on an upper surface of the cover member 2 in the first embodiment, but it is not limited to the convex lens 4, and can be Fresnel lens.

In this embodiment, owing to the provision of the convex lens 4 the interior can be observed on a larger scale, and the flocculation degree of the reaction liquid can be determined more clearly.

Figure 16:
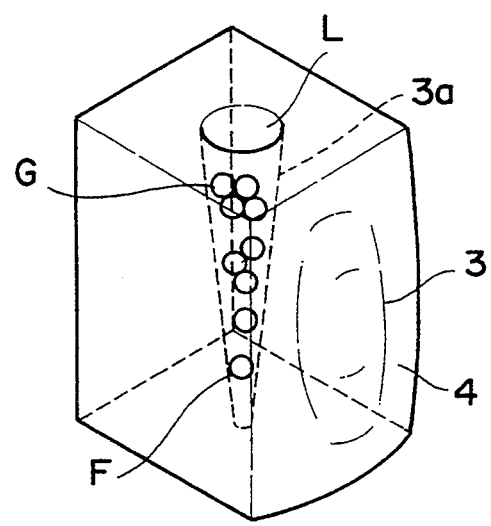
FIG. 16 is a perspective view of a sixth embodiment.
Figure 17:
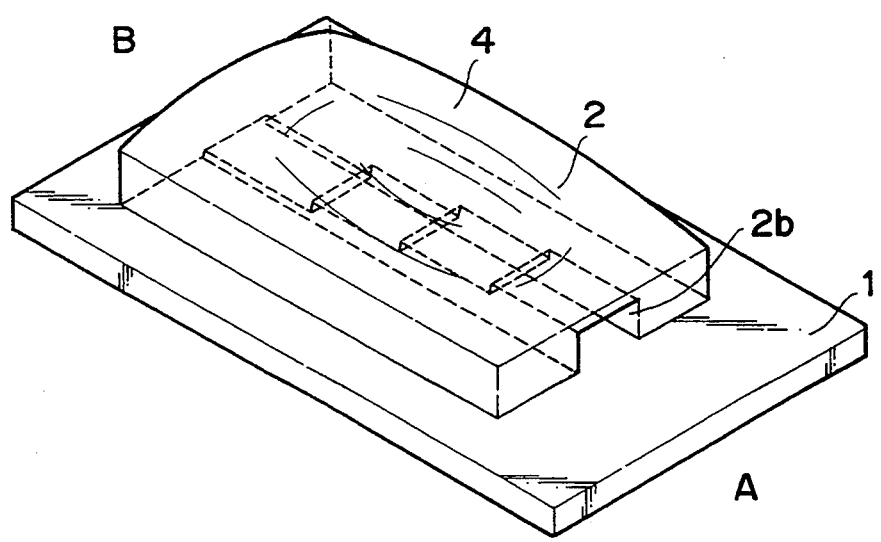
FIG. 17 is a perspective view of a seventh embodiment.
Figure 18:
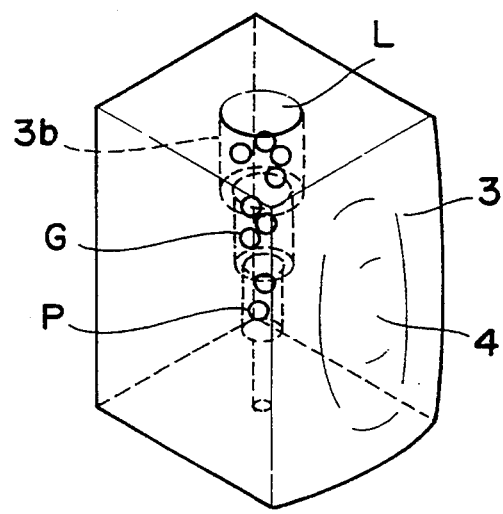
FIG. 18 is a perspective view of an eighth embodiment.
Figure 19:
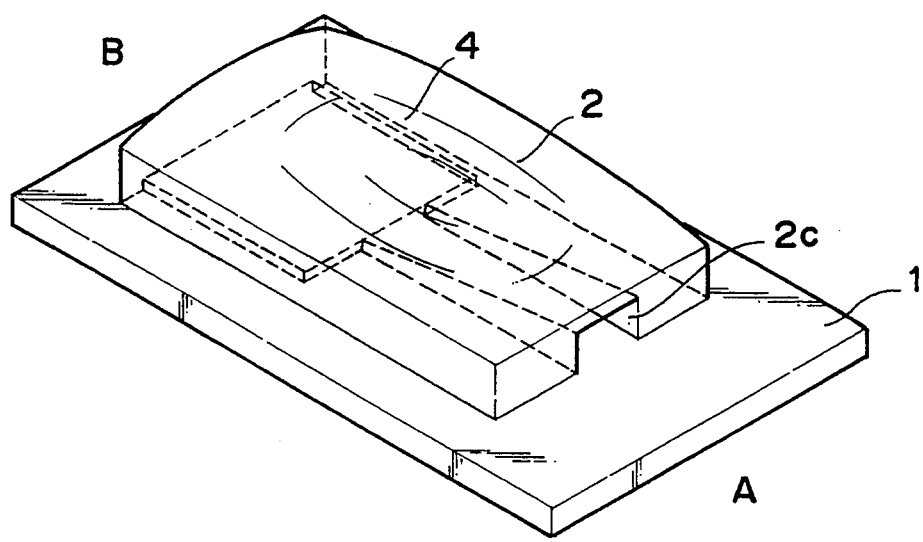
FIG. 19 is a perspective view of a ninth embodiment.

FIG. 16 is a view of the sixth embodiment in which the convex lens 4 is formed on the base body 3 shown in FIG. 4. FIGS. 17, 18 and 19 are views of seventh, eighth and ninth embodiments in which the convex lens 4 is formed on each base body 3 shown in FIG. 5, FIG. 8 and FIG. 9, respectively. Thus the reaction liquid can be observed more clearly through the convex lens 4.

Figure 20:
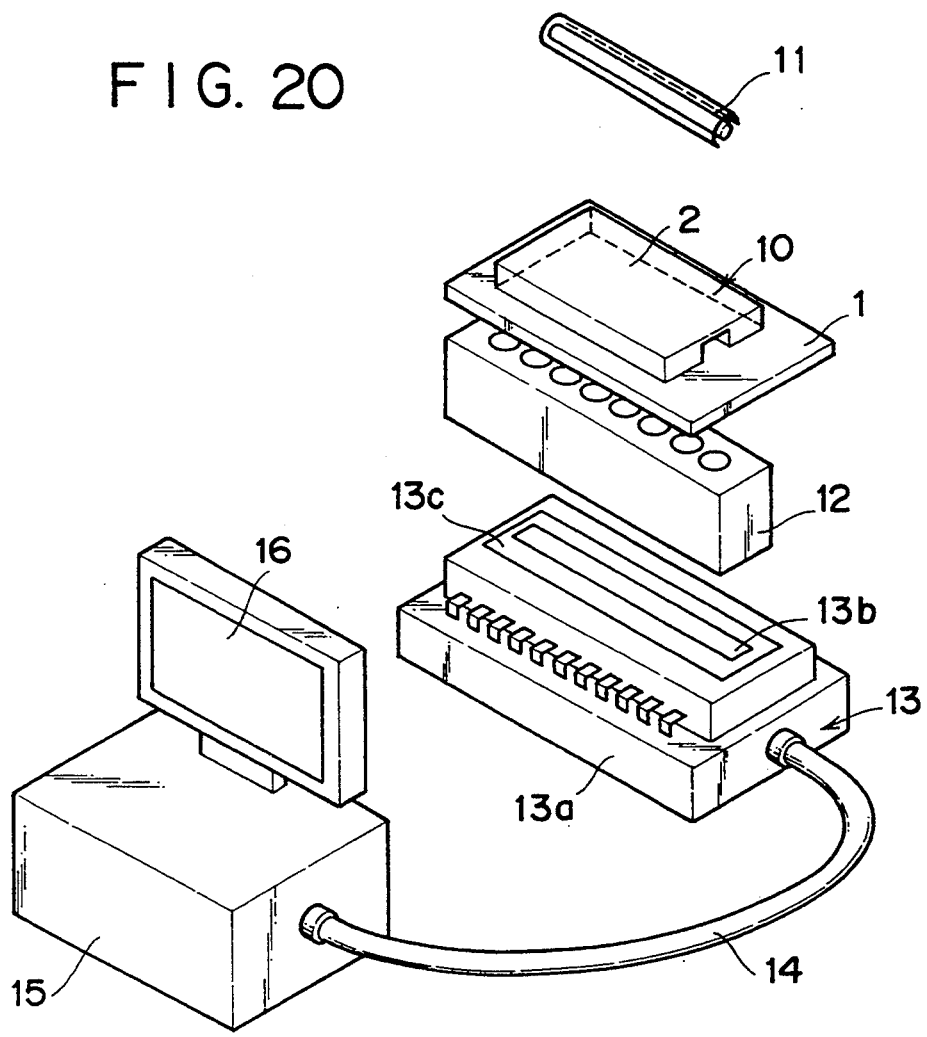
FIG. 20 is a perspective view of a tenth embodiment.
Figure 21:
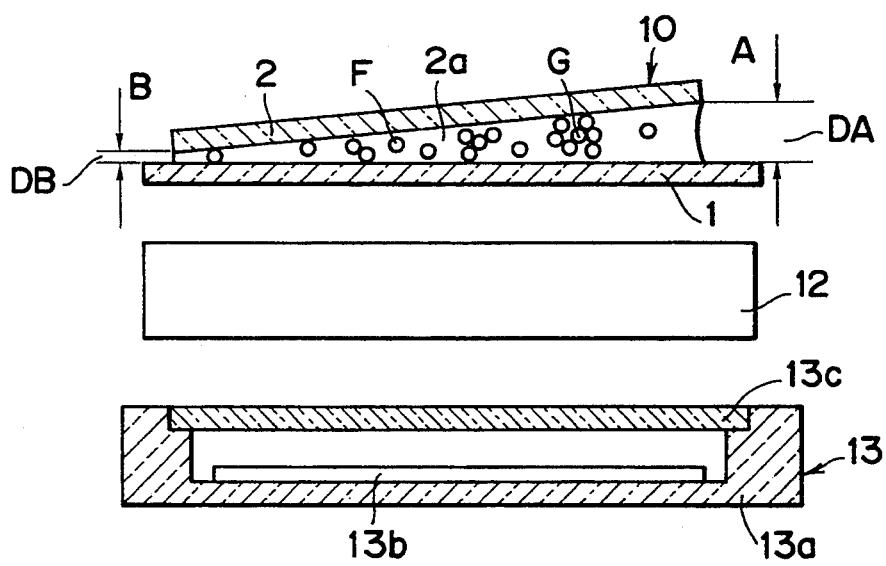
FIG. 21 is a cross-sectional view of an optical system portion in the tenth embodiment.

FIG. 20 shows a constitutional view of the tenth embodiment for automatically reading the state of reaction liquid and FIG. 21 shows a cross-sectional view of an optical system. A sample stand 10 used herein is the same as in the first embodiment.

In order to detect optically the fluorescent carrier particles F poured into the clearance of the sample stand 10, a light source 11 for exciting the flourescent carrier particles via a band path filter is arranged above the sample stand 10, and an image forming optical system 12 comprising an imaging lens and a distributed index lens is arranged below the sample stand 10. A light receiving optical system 13 is provided at its image focusing position. The light receiving optical system 13 has a CCD array 13b having linearly arranged 2048 photosensitive elements of 14 $\mu$m $\times$ 14 $\mu$m. The array 13b is protected by a transparent glass protective plate 13c attached to a frame 13a. The output of each photosensitive element in the CCD array 13b is connected via a cable 14 to a signal processor 15. The output of the signal processor 15 is connected to a monitor 16.

Figure 22:
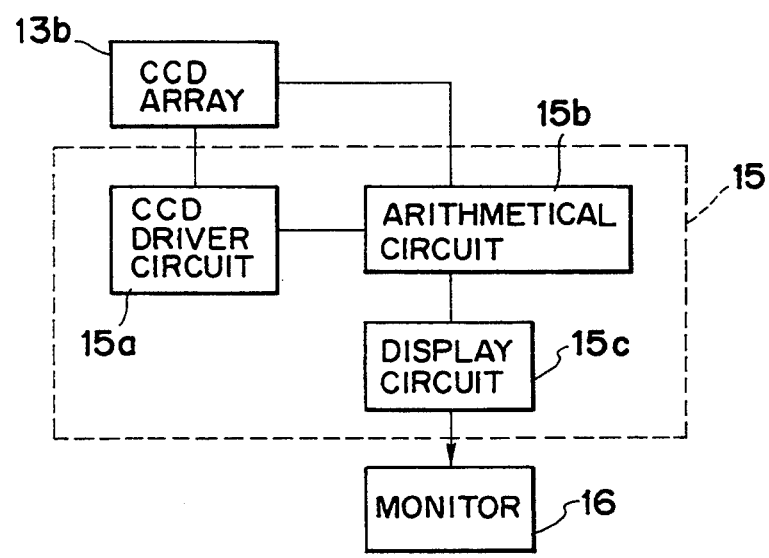
FIG. 22 is a constitutional view of a signal processing apparatus in the tenth embodiment.

The constitution within the signal processor 15 is shown in FIG. 22, wherein the output of the CCD array 13b is connected to a CCD driver circuit 15a and an arithmetical circuit 15b, the output of the CCD driver circuit 15a is connected to the arithmetical circuit 15b. The output of the arithmetical circuit 15b is connected to a display circuit, and the output of the display circuit 15c is connected to the monitor 16.

Figure 23A:
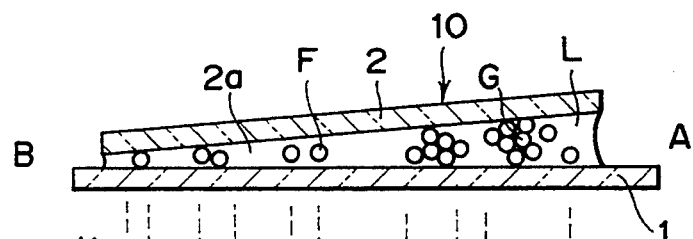
FIGS. 23A and 23B are explanation views of an optical measuring principle in the tenth embodiment.

When an immunological active substance such as monoclonal antibody is caused to sensitize carrier particles F emitting the fluorescence, and a reagent having the carrier particles F dispersed into a liquid medium mainly composed of the water is mixed with the specimen such as serum, the reaction will occur in which the flocculate G is formed from plural immunological active substances and carrier particles F. After sufficient reaction, if this reaction liquid L is poured into a clearance between the board 1 and the recess 2a from the direction A, as shown in FIG. 23A, the reaction liquid L enters in the direction B having a narrower vertical spacing due to surface tension. A single carrier particle F unflocculated can move deep into the direction B because it is small in diameter, while the flocculate G is trapped on its way and can not move because of its size.

A fluorescent image of the reaction liquid L within the recess 2a of the sample stand 10 is formed on the CCD array 13b of the light receiving optical system 13 by the image forming optical system 11, and converted photoelectrically by the CCD driver circuit 15a, wherein the output voltage value of each photosensitive element is input into the arithmetical circuit 15b.

Figure 23B:
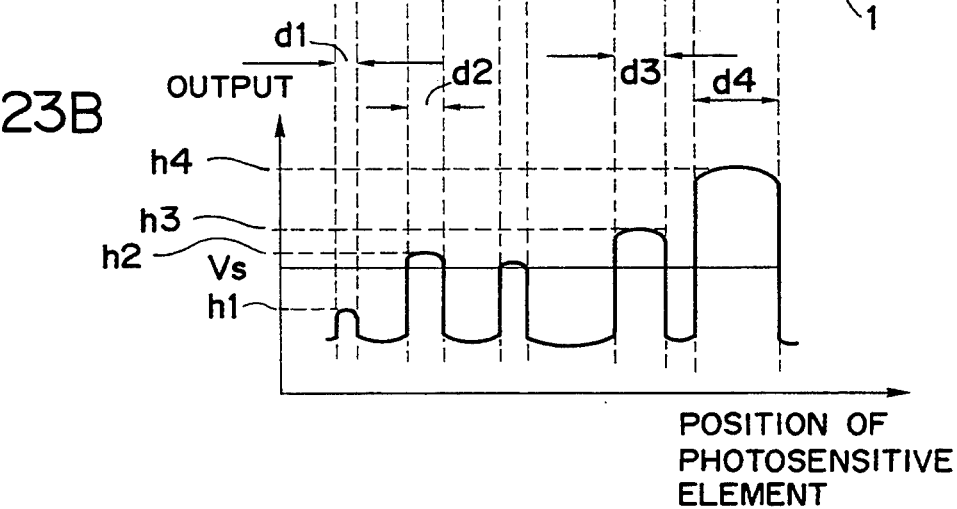

FIG. 23B shows the output voltage of each photosensitive element corresponding to a separated image as shown in FIG. 23A. Due to the fluorescence emitted from the carrier particle F and the flocculate G, the output voltage is increased at the position where they are trapped, thereby detecting their presence.

In practice, an analytical curve is made beforehand by the reaction liquid L reacted with a specimen for analysis containing a known immunological active substance, and the determination is made by comparison with that curve. The operation of the arithmetical circuit 15b is to compare the distribution of the magnitude h1, h2, h3, h4, and the width d1, d2, d3, d4, for the peak of the output voltage with that of the analytical curve, for example. Or more simply, the comparison can be made by counting the number of photosensitive elements where the power voltage value is higher than the threshold voltage Vs. Its processing method is not limited to the above method, and the arithmetical processing result is displayed on the monitor 16 through the display circuit 15c.

Figure 24:
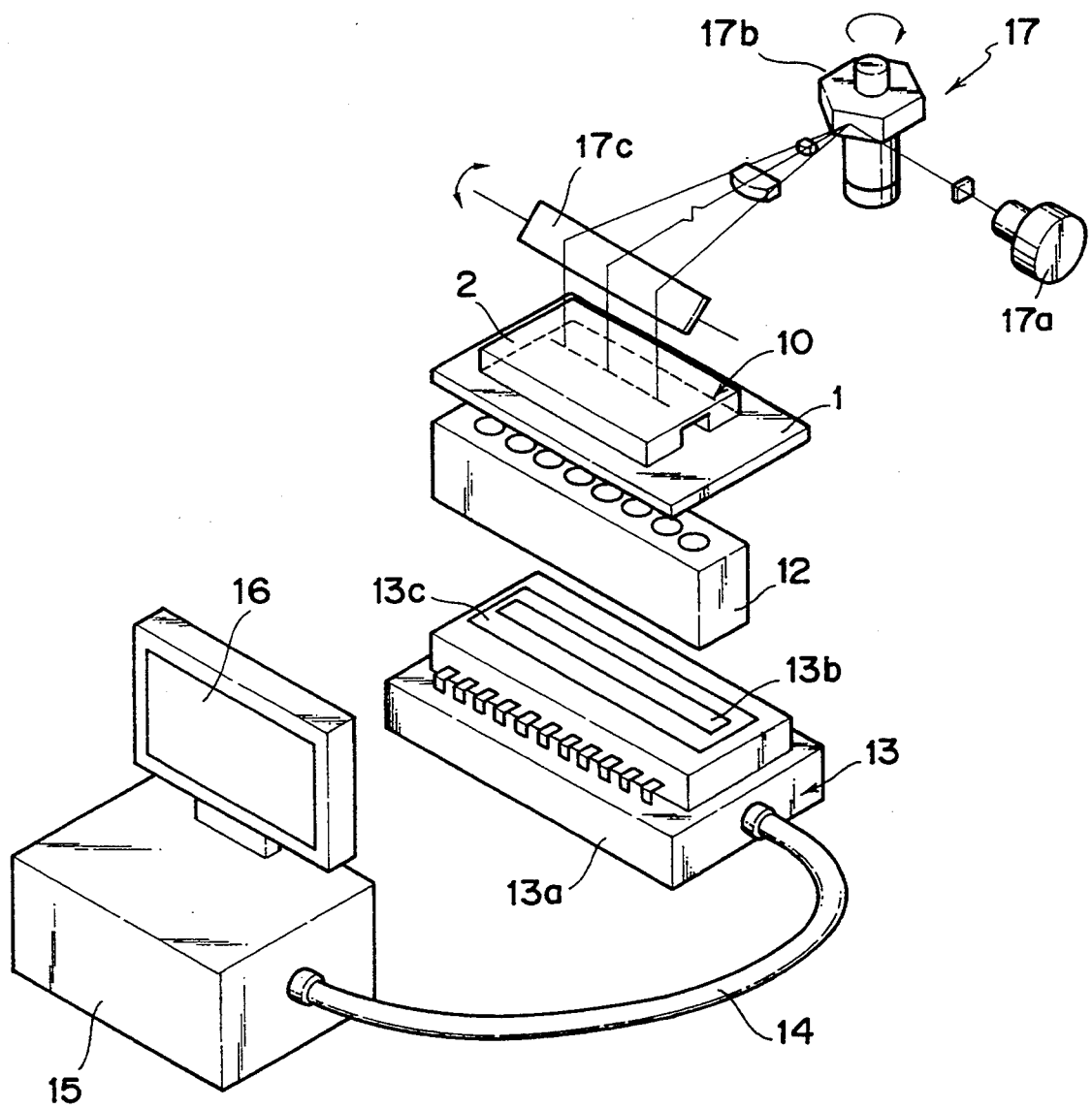
FIG. 24 is a perspective view of a modification of the tenth embodiment using a laser scanning optical system.

FIG. 24 is a modification of the tenth embodiment, wherein a laser scan optical system 17 is used instead of the light source 9, and the laser beam emitted from a laser light source 17a is deflectively scanned by a polygonal mirror 17b to illuminate the reaction liquid within the sample stand 10 from a movable reflection mirror 17c.

Figure 25:
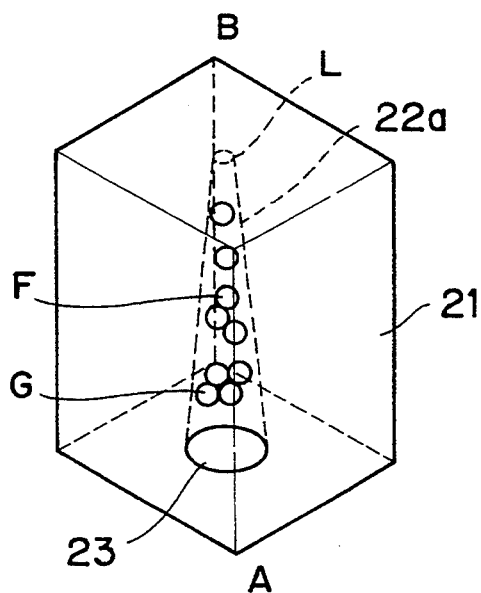
FIG. 25 is a perspective view of an eleventh embodiment.
Figure 26:
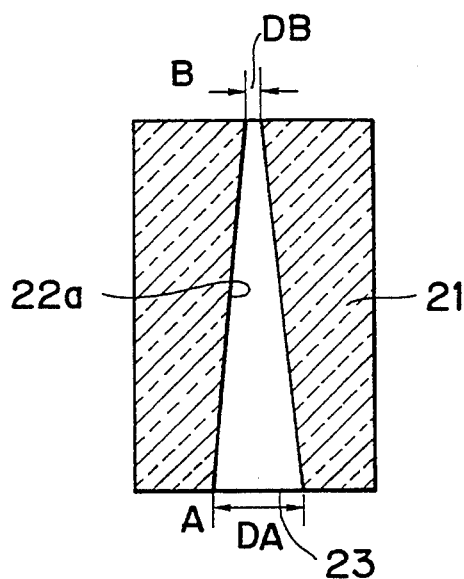
FIG. 26 is a longitudinal cross-sectional view of FIG. 25.

FIG. 25 is a perspective view of the eleventh embodiment, and FIG. 26 is a longitudinal cross-sectional view taken along the direction A–B of FIG. 25. In FIG. 25, there is formed a conical clearance 22a having the diameter continuously increasing in a downward direction within a base body 21 which is partially or totally transparent.

Figure 27:
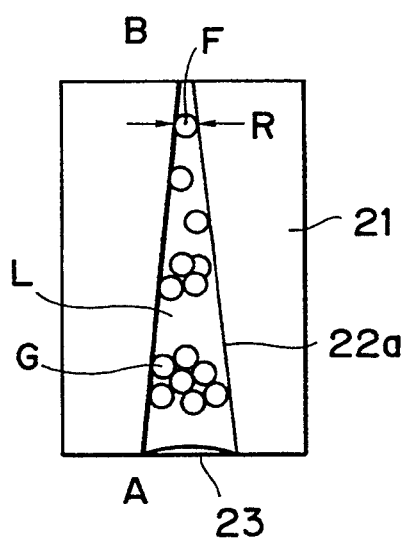
FIG. 27 is an explanation view of a measuring principle in the eleventh embodiment.

As shown in FIGS. 26 and 27, the clearance DB of an opening at an upper end portion of the base body 21 is made smaller than the diameter R of carrier particle F to be used, and the clearance DA of an opening at a lower end portion is about several to hundreds times the clearance DB so that the flocculate G formed by aggregative carrier particles F can pass therethrough.

An immunological active substance such as a monoclonal antibody is caused to sensitize carrier particles F having a smaller specific gravity than the liquid of a specimen, and a reagent having the carrier particles F dispersed into a liquid medium mainly composed of the water is mixed with the specimen such as serum. Then, the antigen-antibody reaction will occur if there exists any antigen specifically reacting to the monoclonal antibody in the serum, wherein the flocculate G is formed from plural immunological active substances and carrier particles F. After sufficient reaction, this reaction liquid L is poured from an opening portion 23 provided in a lower side, as shown in FIG. 27, to fill the clearance 22a. Then, since the specific gravity of the carrier particle F is lighter than that of the liquid of specimen, the carrier particle F and the flocculate G will float upward in the reaction liquid. A single carrier particle F unflocculated can move deep or upward into the direction B because it is small in diameter, but the flocculate G is trapped on its way and can not move because of its size.

The diameter of flocculate G determined by the number of carrier particles F constituting one flocculate G and the number of flocculates G trapped in a certain spacing have a correlation with the property and its number of immunological active substances contained in the reaction liquid L, i.e., the flocculation state of flocculate G generated by the reaction. Accordingly, if the reaction liquid L flows into such clearance 22a, the quantity of carrier particles F trapped in the clearance R equal to the diameter R of single carrier particle F, and the position at which the flocculate G is trapped and its quantity can be easily determined and discriminated, whereby the immunological active substance can be detected qualitatively and quantitatively. In practice, an analytical curve is made beforehand by the reaction liquid L reacted with a specimen for analysis containing a known immunological active substance, and the determination is made by comparison with that curve.

Any portion of the board 21 can be an opaque member, or formed of a black or gray material having low brightness if the carrier particle F is white in color, for exmple, so as to facilitate the discrimination. Also, if a substance having a good affinity with the liquid medium of the reaction liquid L is coated on a surface of the clearance so that the reaction liquid L can easily enter the clearance 22a, a further excellent measuring result can be obtained. This coating material is preferably a phydrophilic substance, a surfactant, or a water-soluble high polymer such as methylcellulose, carboxymethylcellulose, polyvinyl alcohol and polyacrylamide, if the liquid medium is water, for example.

In this case, the clearance DB can be set slightly larger than the diameter of carrier particle F, for example, less than about two times. Then, unflocculated particles or carrier particles F are not trapped but absorbed into the clearance portion SB, so that the flocculation or nonflocculation can be Judged more clearly and easily, and a further excellent measurement result can be obtained.

Figure 28:
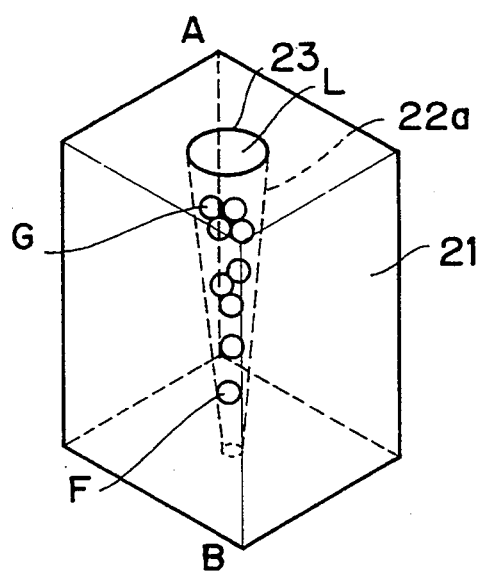
FIG. 28 is a perspective view of a modification of the eleventh embodiment.

In a modification as shown in FIG. 28, the carrier particle F having a heavier specific gravity than the liquid of specimen is used, and a clearance 22a having the diameter decreasing continuously in a downward direction is formed within a base body 21. When an immunological active substance is caused to sensitize the carrier particles F having a heavier specific gravity than the liquid of specimen, and a reagent having the carrier particles F dispersed into a liquid medium mainly composed of the water is mixed with the specimen, the reaction will occur, wherein the flocculate G is formed from plural immunological active substances and carrier particles F. After sufficient reaction if the reaction liquid L is poured from an opening portion 23 at an upper end to fill the clearance 22a. Then, since the specific gravity of the carrier particle F is a heavier than that of the liquid of the specimen, the carrier particle A and the flocculate G will sink down in the reaction liquid. A single carrier particle F unflocculated can move deep into the lower direction because it is small in diameter, but the flocculate G is trapped on its way and can not move because of its size.

Figure 29:
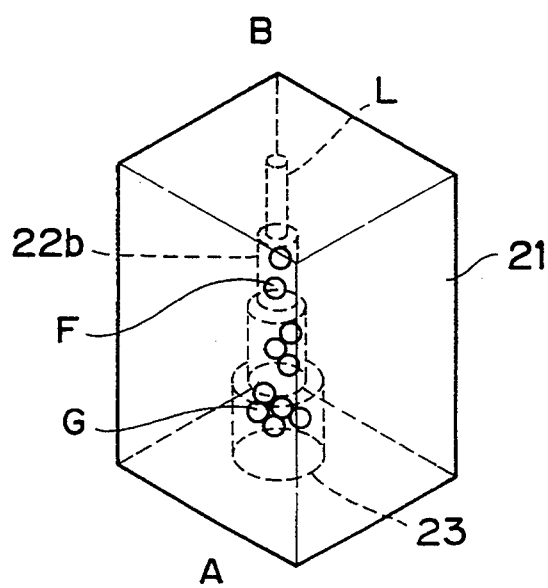
FIG. 29 is a perspective view of a twelfth embodiment.
Figure 30:
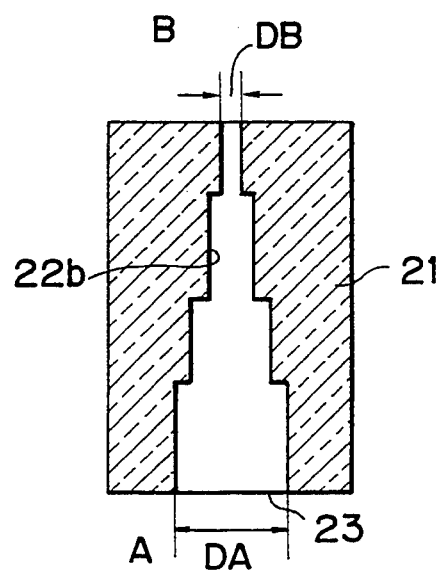
FIG. 30 is a longitudinal cross-sectional view of FIG. 29.
Figure 31:
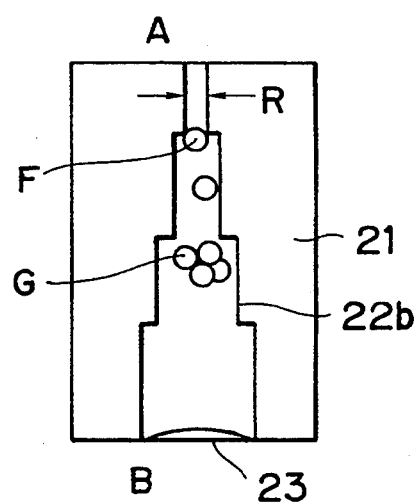
FIG. 31 is an explanation view of a measuring principle in the twelfth embodiment.

FIG. 29 is a constitutional view of the twelfth embodiment, and FIG. 30 is a longitudinal cross-sectional view taken along the direction A–B. On a base body 21, which is partially or totally transparent, is formed a clearance 22b having the diameter increasing in four steps toward the lower direction. As shown in FIGS. 30 and 31, the vertical spacing DB of an opening at an upper end portion is made smaller than the diameter of carrier particle F for use, and the vertical spacing DA of an opening portion 23 at a lower end portion is about several to hundreds times the vertical spacing DB so as to pass the flocculate G therethrough.

In this embodiment, the reaction liquid L is poured from the opening portion 23 to fill the clearance 22b. Then, since the specific gravity of the carrier particle F is lighter than that of the liquid of the specimen, the carrier particle F and the flocculate G will float upward in the reaction liquid. The immunological active substance can be similarly detected qualitatively and quantitatively, because the flocculate G is trapped on its way, as shown in FIG. 31. For its purpose, the vertical spacing of the recess 22b must be changed at least in three steps.

Figure 32:
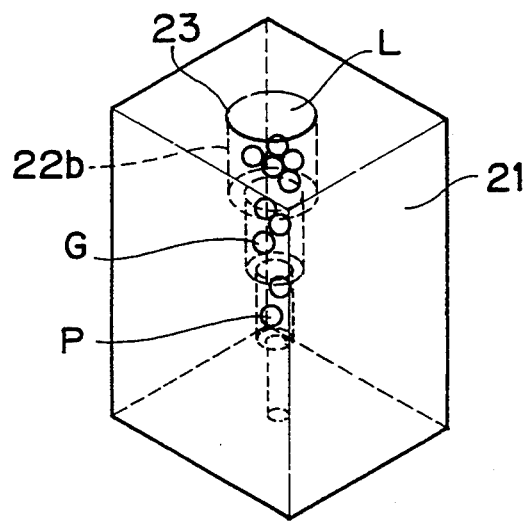
FIG. 32 is a perspective view of a modification of the twelfth embodiment.

Also, FIG. 32 is a modification, wherein a base body 21 is formed with a clearance 22b having the diameter decreasing in four steps toward the lower direction. In this case, the carrier particle F having a heavier specific gravity than the liquid of the specimen is used as shown in FIG. 28.

Figure 34:
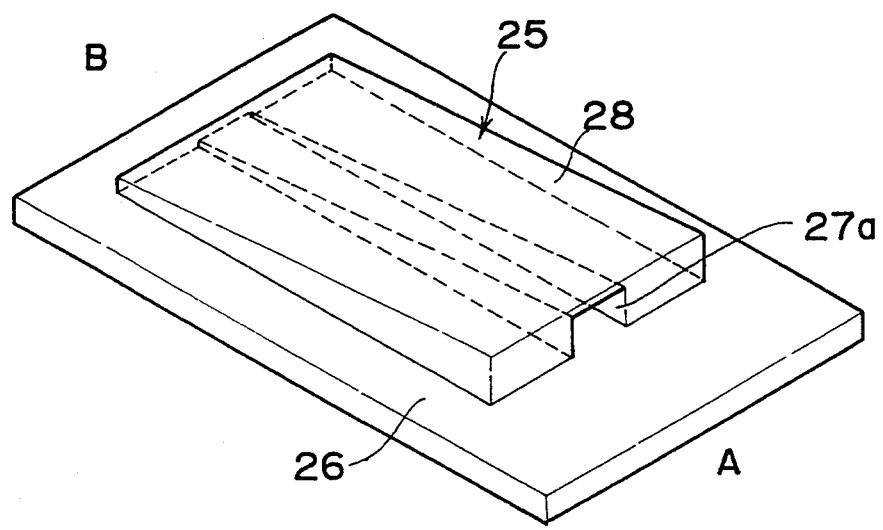
FIG. 34 is a perspective view of a sample stand available in FIG. 33.

FIG. 33 is a plan view of the thirteenth embodiment for exerting centrifugal force, and FIG. 34 is a perspective view of a sample stand to be used. In FIG. 33, four sample stands 25 are disposed on a rotation plate 24. The sample stand 25 comprises a slab-like board 26 of a transparent material closely attached a wedge-shaped cover member 28 formed of a transparent material and provided with a recess 27a in a central inner portion, as shown in the longitudinal cross-sectional view of FIG.

35, thereby to form a clearance. The recess 27a is such that the height of clearance from the board 26 decreases continuously from the direction A to the direction B, with the vertical spacing DB of an opening at an end portion being smaller than the diameter R of a carrier particle F for use, and the vertical spacing DA of an opening at a directional end portion being about several to hundreds times the vertical spacing DB so as to pass the flocculate G therethrough.

Figure 36:
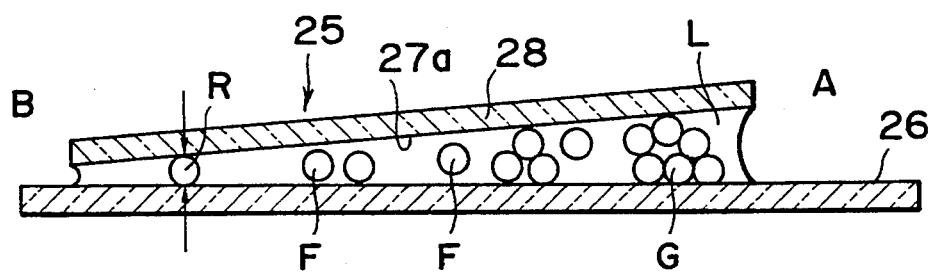
FIG. 36 is an explanation view of a measuring principle in the thirteenth embodiment.

When an immunological active substance such as a monoclonal antibody is caused to sensitize carrier particles F, and a reagent having the carrier particles F dispersed into a liquid medium mainly composed of the water is mixed with a specimen having a lighter specific gravity than the carrier particle F, the reaction will occur in which the flocculate G is formed from plural immunological active substances and carrier particles F. After sufficient reaction, this reaction liquid L is poured into the clearance between the board 26 and the recess 27a from the direction A, as shown in FIG. 36.

The sample stands 25 are placed on the rotation plate 24 with the side A located inward, as shown in FIG. 33, and the rotation plate 24 is rotated around a rotation center. Owing to the centrifugal force of this rotation, the carrier particle F having a greater specific gravity enters the reaction liquid L in the direction B having a narrower vertical spacing, as shown in FIG. 36. A single carrier particle F unflocculated can move deep into the direction B because it is small in diameter, but the flocculate G is trapped on its way and can not move because of its size.

Figure 37:
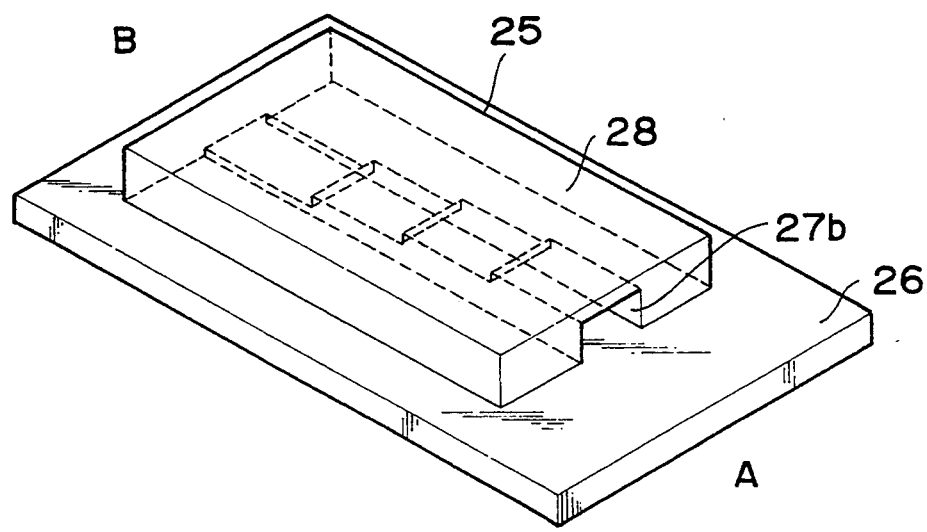
FIG. 37 is a perspective view of a modification of the sample stand of FIG. 34.
Figure 38:
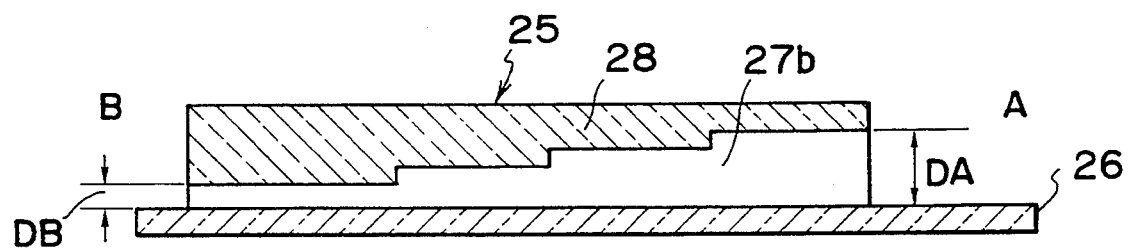
FIG. 38 is a longitudinal cross-sectional view of the sample stand of FIG. 37.
Figure 39:
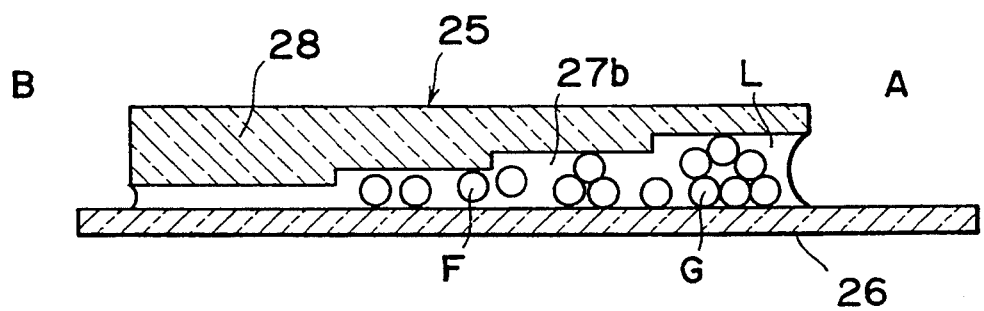
FIG. 39 is an explanation view of a measuring principle of a modification of FIG. 37.

FIG. 37 is a perspective view of a modification of the sample stand 25, and FIG. 38 is a londitudinal cross-sectional view taken along the direction A-B of FIG. 37. On a board 6 is closely attached a cover member 28 provided with a recess 27b in a central inner portion, thereby to form a clearance. The recess 27b is such that the height of the clearance from the board 26 decreases in four steps from the direction A to the direction B, with the vertical spacing DB of an opening at an end portion in the direction B being smaller than the diameter R of a carrier particle F for use, and the vertical spacing DA of an opening at an end portion in the direction A being abut several to hundreds times the vertical spacing DB so as to pass the flocculate G therethrough.

In this modification, when the reaction liquid L containing the carrier particle F having a different specific gravity is poured from the direction A, and the centrifugal force is exerted by the rotation plate 24, the immunological active substance can be similarly detected qualitatively and quantitatively, because the flocculate G is trapped on its way as shown in FIG. 37. For its purpose, the vertical spacing of the recess 27b must be changed at least in three steps.

Figure 40:
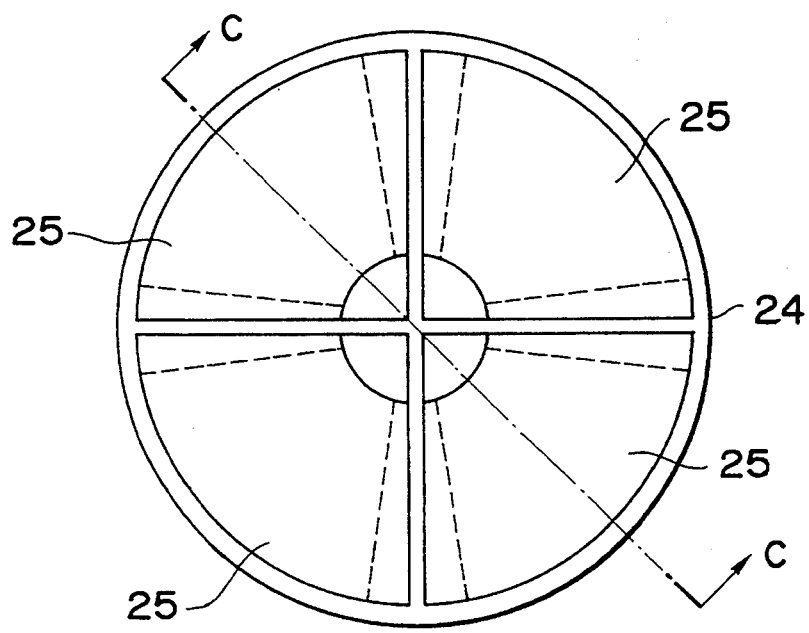
FIG. 40 is a plan view of a fourteenth embodiment.
Figure 41:
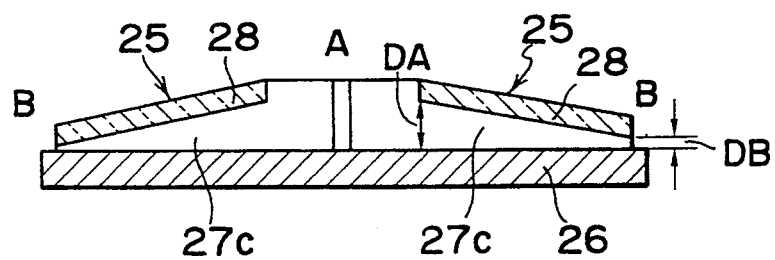
FIG. 41 is a cross-sectional view taken along line C—C of FIG. 40.

FIG. 40 is a plan view of the fourteenth embodiment, and FIG. 41 is a longitudinal cross-sectional view taken along the direction C—C of FIG. 40. On a disk-like board 26 formed of a transparent material is provided a sample stand 25 which is divided into four sections, and includes a cover member 28 to have a clearance formed by a recess 27c. The recess 27c is such that the height of the clearance from the board 26 decreases continuously from the central portion toward the outward direction, with the vertical spacing DB of an opening at an outward portion being smaller than the diameter R of carrier particles F for use, and the vertical spacing DA of an opening at an inner portion being about several to hundreds times the vertical spacing DB so as to pass the flocculate G therethrough.

Figure 35:
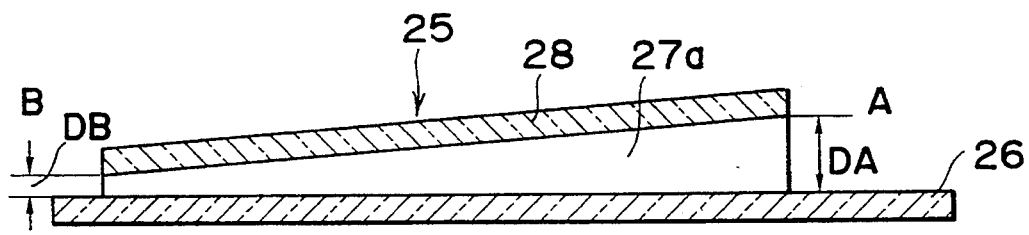
FIG. 35 is a longitudinal cross-sectional view of FIG. 34.

This division is not particularly defined as four but any number of divisions or no division can be configured to facilitate the measurement. Furthermore, the configuration in cross section as shown in FIG. 41 is based on FIG. 35, but can be based on FIG. 38.

Figure 42:
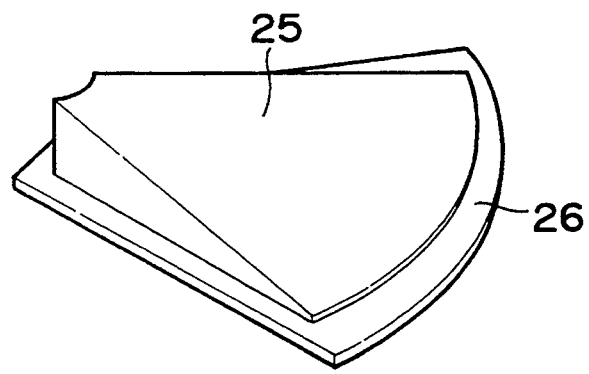
FIG. 42 is a perspective view of a modification in the fourteenth embodiment.

Also, the board 26 itself can be divided as shown in FIG. 42.

As above described, the specimen measuring apparatus has a simple structure with the clearance decreasing continuously or in steps from a maximum spacing sufficiently larger than the diameter of the carrier particle, and when the reaction liquid is poured from an opening of maximum spacing into this clearance, the carrier particle and the flocculate which are different in size can be separated due to the difference of spacings, so that the immunological active substance in the specimen can be detected qualitatively and quantitatively at high precision.

What is claimed is:

1. An apparatus for measuring a specified substance in a specimen by flocculation of carrier particles in a reaction liquid of the specimen, with the carrier particles carrying a substance that specifically binds with the specified substance, comprising:

a container having a first opening with a spacing larger than a diameter of the individual carrier particles and a second opening opposite the first opening with a spacing smaller than a diameter of the individual carrier particles, wherein an interior clearance portion extending along a vertical direction of said container connects the first and second openings, with said interior clearance portion having either one of a tapered shape with spacing continuously decreasing or a stepwise shape with spacing decreasing in step-by-step increments from the first opening toward the second opening, wherein the reaction liquid enters from the first opening and a flocculate of the carrier particles is trapped in a space along the interior clearance portion corresponding to a size of the flocculate, and wherein the carrier particles have a different specific gravity than the reaction liquid.

2. An apparatus according to claim 1, wherein the carrier particles have a larger specific gravity than the reaction liquid.

3. An apparatus according to claim 1, wherein said container includes at least one surface surrounding the clearance portion that includes a transparent portion.

4. An apparatus according to claim 4, wherein said transparent portion has a lens effect.

5. An apparatus according to claim 1, wherein the carrier particles are colored particles or fluorescent particles.

6. An apparatus according to claim 1, wherein the specified substance is an antigen, and the carrier particles carry a monoclonal antibody specifically reacting with the antigen.

7. An apparatus for measuring a specified substance in a specimen by flocculation of carrier particles in a reaction liquid of the specimen, with the carrier particles carrying a substance that specifically binds with the specified substance, comprising:

a container having a first opening with a spacing larger than a diameter of the individual carrier particles and a second opening opposite the first opening with a spacing smaller than a diameter of the individual carrier particles wherein an interior clearance portion extending along a vertical direction of said container connects the first and second openings, with said interior clearance portion having either one of a tapered shape with spacing continuously decreasing or a stepwise shape with spacing decreasing in step-by-step increments from the first opening toward the second opening, wherein the reaction liquid enters from the first opening and a flocculate of the carrier particles is trapped in a space along the interior clearance portion corresponding to a size of the flocculate, and wherein the carrier particles have a different specific gravity than the reaction liquid; and a detector for detecting the flocculates of carrier particles trapped in the clearance portion.

8. An apparatus according to claim 7, wherein said detector includes optical detection means.

9. An apparatus according to claim 8, wherein said optical detection means includes an array comprising light receiving elements.

10. An apparatus according to claim 7, wherein the carrier particles have a larger specific gravity than the reaction liquid.

11. An apparatus according to claim 7, wherein said container includes at least one surface surrounding the clearance portion that includes a transparent portion.

12. An apparatus according to claim 11, wherein said transparent portion has a lens effect.

13. An apparatus according to claim 7, wherein the carrier particles are colored particle or fluorescent particles.

14. An apparatus according to claim 7, wherein the specified substance is an antigen and, the carry particles carries a monoclonal antibody specifically reacting with the antigen.

15. A method for measuring a specified substance in a specimen by flocculation of carrier particles in a reaction liquid of the specimen, with the carrier particles carrying a substance that specifically binds with the specified substance, comprising the steps of:

flowing the reaction liquid into a container having a first opening with a spacing larger than a diameter of the individual carrier particles and a second opening opposite the first opening with a spacing smaller than a diameter of the individual carrier particles, wherein an interior clearance portion extending along a vertical direction of said container connects the first and second openings, with said interior clearance portion having either one of a tapered shape with spacing continuously decreasing or a stepwise shape with spacing decreasing in step-by-step increments form the first opening toward the second opening, wherein the reaction liquid enters from the first opening and a flocculate of the carrier particles is trapped in a space along the interior clearance portion corresponding to a size of the flocculate, wherein the carrier particles have a different specific gravity than the reaction liquid;

moving the carrier particles by using the difference of the specific gravity in a direction in which the spacing of the clearance portion decreases; and detecting a position where the flocculates of carrier particles in the reaction liquid have been trapped in the clearance portion.

16. A method according to claim 15, wherein the carrier particles have a larger specific gravity than the reaction liquid.

17. A method according to claim 15, wherein the carrier particles are colored particle or fluorescent particles.

18. A method according to claim 15, wherein the specified substance is an antigen and, the carry particles carries a monoclonal antibody specifically reacting with the antigen.

19. An apparatus for measuring a specified substance in a specimen by flocculation of carrier particles in a reaction liquid of the specimen, with the carrier particles carrying a substance that specifically binds with the specified substance, comprising:

a container having a first opening with a spacing larger than a diameter of individual carrier particles, with said container having a second opening provided opposite to the first opening with a spacing smaller than a diameter of the individual carrier particles, with said container having an interior clearance portion extending along a vertical direction of said container connecting the first and second openings and having either one of a tapered shape with spacing continuously decreasing or a stepwise shape with spacing decreasing in step-by-step increments from the first opening toward the second opening, with said container having a liquid accumulation room connected to the second opening for accumulating the reaction liquid therein, the liquid accumulation room having a volume greater than that of the clearance portion, wherein the reaction liquid enters from the first opening and exits through the second opening to the liquid accumulation room, and a flocculate of the carrier particles in the reaction liquid is trapped in a space along the interior clearance portion corresponding to a size of the flocculate.

20. An apparatus according to claim 19, further comprising a detector for detecting the carrier particles trapped in the clearance portion.

* * * * *

UNITED STATES PATENT AND TRADEMARK OFFICE
CERTIFICATE OF CORRECTION

PATENT NO. : 5,427,959
DATED : June 27, 1995
INVENTOR(S) : Nishimura et al.

It is certified that error appears in the above-indentified patent and that said Letters Patent is hereby corrected as shown below:

[57] ABSTRACT:

Line 11, "the" should be deleted.

COLUMN 7:

Line 65, "phydrophilic" should read --hydrophilic--.

COLUMN 10:

Line 52, "claim 4," should read --claim 3,--.

COLUMN 11:

Line 32, "particle" should read --particles--.
Line 35, "antigen and," should read --antigen, and-- and "carry" should read --carrier--.
Line 36, "carries" should read --carry--.
Line 54, "form" should read --from--.

UNITED STATES PATENT AND TRADEMARK OFFICE
CERTIFICATE OF CORRECTION

PATENT NO. : 5,427,959
DATED : June 27, 1995
INVENTOR(S) : Nishimura et al.

It is certified that error appears in the above-indentified patent and that said Letters Patent is hereby corrected as shown below:

COLUMN 12:

Line 16, "particle" should read --particles--.
Line 19, "antigen and," should read --antigen, and-- and "carry" should read --carrier--.
Line 20, "carries" should read --carry--.

Signed and Sealed this

Twelfth Day of December, 1995

Attest:

BRUCE LEHMAN

Attesting Officer

Commissioner of Patents and Trademarks